(12) United States Patent
Prewer

(10) Patent No.: US 11,529,603 B2
(45) Date of Patent: Dec. 20, 2022

(54) ELONGATE SOLID PHASE BODY

(71) Applicant: Swedish Biomimetics 3000 Ltd, Norwich (GB)

(72) Inventor: Andrew Prewer, Norwich (GB)

(73) Assignee: Swedish Biomimetics 3000 LTD, Norwich (GB)

( * ) Notice: Subject to any disclaimer, the term of this patent is extended or adjusted under 35 U.S.C. 154(b) by 431 days.

(21) Appl. No.: 16/461,648

(22) PCT Filed: Nov. 20, 2017

(86) PCT No.: PCT/GB2017/053480
§ 371 (c)(1),
(2) Date: May 16, 2019

(87) PCT Pub. No.: WO2018/096321
PCT Pub. Date: May 31, 2018

(65) Prior Publication Data
US 2019/0351385 A1   Nov. 21, 2019

(30) Foreign Application Priority Data

Nov. 22, 2016   (GB) ..................................... 1619713

(51) Int. Cl.
*B01J 19/00* (2006.01)
*C07K 1/04* (2006.01)

(52) U.S. Cl.
CPC .......... *B01J 19/0046* (2013.01); *C07K 1/045* (2013.01); *C07K 1/047* (2013.01); *B01J 2219/00295* (2013.01); *B01J 2219/00461* (2013.01); *B01J 2219/00518* (2013.01); *B01J 2219/00722* (2013.01); *B01J 2219/00725* (2013.01)

(58) Field of Classification Search
None
See application file for complete search history.

(56) References Cited

U.S. PATENT DOCUMENTS

| | | | |
|---|---|---|---|
| 4,631,211 A | 12/1986 | Houghten | |
| 5,235,028 A | 8/1993 | Barany et al. | |
| 7,338,768 B1 * | 3/2008 | Trau ....................... | C07K 1/047 435/7.1 |
| 2004/0058391 A1 | 3/2004 | Baum | |

FOREIGN PATENT DOCUMENTS

| | | |
|---|---|---|
| EP | 2162208 A1 | 3/2010 |
| NL | 1006813 C1 | 1/1998 |
| WO | 9932705 A2 | 7/1999 |

(Continued)

OTHER PUBLICATIONS

International Preliminary Report on Patenability for PCT Application PCT/GB2017/053480 dated Jun. 6, 2019.
(Continued)

*Primary Examiner* — Christopher M Gross
(74) *Attorney, Agent, or Firm* — Troutman Pepper Hamilton Sanders LLP; Ryan A. Schneider

(57) ABSTRACT

An elongate solid phase body suitable for performing solid phase synthesis. The solid phase body includes a plurality of enclosures formed of a material of a chemically inert mesh and, within each enclosure, a plurality of solid phase beads.

21 Claims, 2 Drawing Sheets

(56) References Cited

FOREIGN PATENT DOCUMENTS

Figure 1:
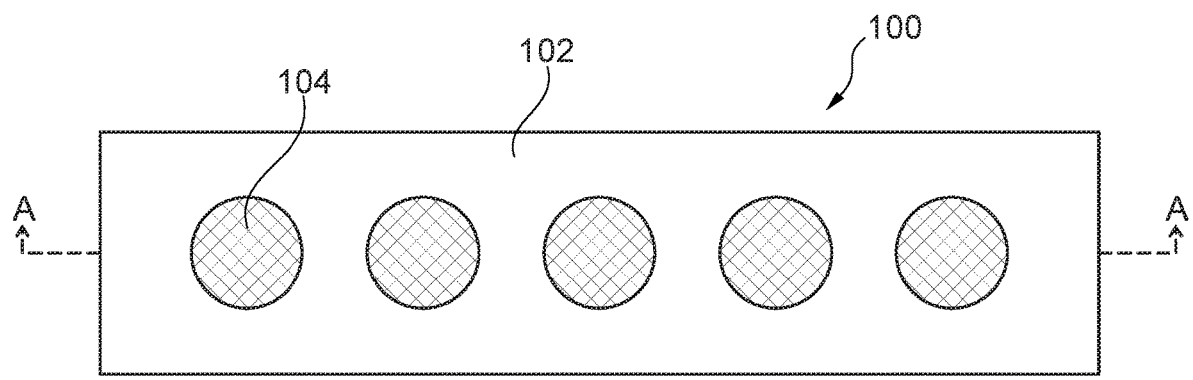

WO         0015653 A2    3/2000
WO    2009004344 A1    1/2009

OTHER PUBLICATIONS

Bouillon, I. et al., "Resin Capsules: Permeable Containers for Parallel/Combinatorial Solid-Phase Organic Synthesis," J. Comb. Chem., 2008, pp. 714-720, vol. 10, American Chemical Society.
International Search Report and Written Opinion issued in PCT/GB2017/053480 dated Jan. 19, 2018.
European Search Report issued in GB1619713.9 dated Jul. 20, 2017.

* cited by examiner

ELONGATE SOLID PHASE BODY

This invention relates to an elongate solid phase body suitable for performing solid phase synthesis.

BACKGROUND

Solid phase synthesis has found broad application in the preparation of useful molecules and in particular in the preparation of useful biopolymers such as peptides and oligonucleotides. Typically, solid phase synthesis involves a linker group being attached to a solid substrate. The starting material in the synthesis is then attached to the linker group and the various reaction steps that form the synthesis comprises are performed on the starting material by treating the solid substrate starting material conjugate with appropriate reactants as solutions. Residual reactants and reaction by-products are easily separated from the product of each reaction step by washing with appropriate solvents as the product of each step remains attached to the solid substrate. Once the synthesis is complete the linker group can be cleaved liberating the desired product, which can then be collected and processed.

WO2009/004334 and WO2010/079349 describe methods and systems for carrying out solid phase synthesis by passing an elongate solid phase through a series of reaction or wash zones, each of which is in the form of a conduit. The elongate solid phases described in these disclosures are continuous ribbons or cords made of a single material that can be woven into the desired elongate form and that also comprises the functional groups to which the linker groups for the solid phase synthesis are attached. Examples include cellulosic materials, such as cotton.

BRIEF SUMMARY OF THE DISCLOSURE

In a first aspect of the invention is provided an elongate solid phase body for solid phase synthesis, the elongate solid phase body comprising:
- an elongate body portion comprising a plurality of enclosures distributed along the length of the elongate body portion, said enclosures being formed of a material comprising a chemically inert mesh; and
- within each enclosure, a plurality of solid phase beads;

wherein the size of the holes in the mesh and the size distribution of the solid phase beads are selected such that the beads do not pass through the mesh.

The term chemically inert is used herein to mean a polymer that is chemically unreactive and/or insoluble in the conditions of the reactions of the solid phase synthesis.

The mesh may be a polymeric mesh, i.e. one formed of a chemically inert polymer. Where the reaction conditions are fairly mild (e.g. not involving the use of strong acids or bases), polymers such as polypropylene, polyethylene, polyester, polyamide (e.g. aramid), and silk would be suitable.

Certain solid phase syntheses involve cleavage of a protein, peptide or polypeptide from a solid phase resin. This typically involves the use of trifluoroacetic acid in an organic solvent. It may be therefore that the chemically inert polymer is unreactive in the presence of trifluoroacetic acid in an organic solvent (e.g. dichloromethane). The polymer may be a fluorinated polymer or copolymer. The polymer may be polytetrafluoroethylene (PTFE) or ethylene tetrafluoroethylene copolymer (ETFE). The polymer may be ETFE. The polymer may be aramid. The polymer may be polyether ether ketone (PEEK).

Alternatively, the mesh may be formed of a material selected from glass fibres, titanium, stainless steel, carbon fibre, graphene.

It may be that the material is formed of the mesh, e.g. the polymeric mesh.

The pores of the mesh are typically large enough to allow the liquid and the reagent to pass unimpeded or substantially unimpeded through the porous bag or tube to the beads inside. The pore size of the porous material may be less than 150 µm, less than 100 µm, less than 50 µm or less than 25 µm. In certain embodiments, the pore size is in the range from 30 to 80 µm, e.g. in the range from 45 to 65 µm.

It may be that the elongate body and the enclosures are formed of the same material. It may be that the elongate solid phase body comprises two elongate strips of the material connected together so as to form the elongate body portion and the plurality of enclosures. The two strips of material may be connected to each other continuously along both longitudinal sides of the elongate body and periodically connected continuously across the transverse width of the elongate body to form the enclosures. The two strips of material may form part of the same piece of material that is folded along a first longitudinal side of the elongate body. The two strips of material may form part of the same piece of material that is tubular, e.g. one formed on a circular loom.

Where the material is a polymeric mesh, it may be welded continuously along both longitudinal sides of the elongate body and periodically welded continuously across the transverse width of the elongate body to form the enclosures. Where the two strips of elongate material form part of the same piece of material that is folded along a first longitudinal side of the elongate body, the material may be welded continuously along a second longitudinal side of the elongate body and periodically welded continuously across the transverse width of the elongate body to form the enclosures.

Alternatively, the material may be sewn, stapled or bonded continuously along both longitudinal sides of the elongate body and sewn, stapled or bonded continuously across the transverse width of the elongate body to form the enclosures. Where the two strips of elongate material form part of the same piece of material that is folded along a first longitudinal side of the elongate body, the material may be sewn, stapled or bonded continuously along a second longitudinal side of the elongate body and periodically sewn or bonded continuously across the transverse width of the elongate body to form the enclosures.

Where the two strips of elongate material form part of the same piece of material that is tubular, the material may be sewn, stapled or bonded continuously across the transverse width of the elongate body to form the enclosures.

The seams or joins along the longitudinal side or sides of the elongate body may be suitable for providing purchase for a roller, allowing the roller to guide and or drive the elongate material. Thus, the seams or joins along the longitudinal side or sides of the elongate body may comprise sprocket holes or raised or depressed lumps or ridges.

The seams or joins may have a width in the range from 2 mm to 10 mm, e.g. in the range from 3 mm to 5 mm.

The solid phase beads are suitable for solid phase synthesis. Thus, a substance can be attached to the beads and a solid phase synthesis can be carried out on that substance.

The solid phase beads may be spherical. The solid phase beads may be irregularly shaped.

The solid phase beads may be polymer beads. The solid phase beads may be a polystyrene, e.g. a polystyrene divinylbenzene hybrid resin. Illustrative examples of polystyrene divinylbenzene hybrid resin include: polysytrene crosslinked with 1-2% divinylbenzene (a 'Merrifield resin') or a Wang resin (but having Wang linker groups) or RINK resin. The solid phase beads may be a polyethylene glycol or a polyethylene glycol copolymer based resin. For example, the solid phase beads may be a polystyrene/polyethylene glycol hybrid resin, e.g. TentaGel™ beads. Alternatively, the solid phase beads may be selected from controlled porosity glass beads, polyamide beads and polyether beads.

The solid phase beads may have linker group precursors attached to them.

The solid phase beads may have a diameter of from 45 to 180 μm, for example from 60 to 180, or from 60 to 100 μm or from 150 to 180 μm.

The elongate body may have a length greater than 500 mm. The elongate body may have a length greater than 1000 mm. The width of the elongate body is typically in the range 5 mm to 100 mm, e.g. 5 to 30 mm. The width of the elongate body may be in the range 15 mm to 25 mm.

The elongate body may be continuous, i.e. it may be in the form of a loop.

The solid phase beads are typically packed in such a way as to allow free movement. This is of benefit when using ultrasound to increase the mixing of a fluid phase and the beads. Thus, it may be that the enclosures are each only partially filled with solid phase beads. It may be that the enclosure contains less than 90% (e.g. less than 80% or less than 70%) of the maximum amount of beads that the enclosure could hold.

The enclosures may have substantially the same transverse width (the dimension of the enclosure in a direction transverse to the elongate body) as the elongate body. There will typically be at least one seam and/or join that runs along the longitudinal edge or edges of the elongate body, said seam or join forming the enclosure. The term 'substantially' in this instance means that the transverse width of the elongate body will be the transverse width of the enclosure plus the sum of the widths of said seam(s) and/or join(s).

The enclosures may have a longitudinal length (the dimension of the enclosure in a direction longitudinal to the elongate body) of between 5 and 50 mm. The enclosures may have a longitudinal length (the dimension of the enclosure in a direction longitudinal to the elongate body) of between 15 and 25 mm.

The enclosures may all be the same size. Alternatively, some enclosures may be smaller than others. This would be useful, for example, for obtaining samples of the solid phase beads at various positions along the elongate membrane, e.g. during operation. It may be there are two groups of enclosures and that the enclosures in each group are the same size as the other enclosures in that group. It may be that the enclosures in a first group are smaller than those in a second group. It may be that less than 20% of the total numbers of enclosures are in the first group. It may be that less than 10% of the enclosures are in the first group. The enclosures of the first group may be situated periodically along the elongate solid phase body.

In a second aspect of the invention is provided a method of performing a solid phase synthesis: the method comprising passing the elongate solid phase body of the first aspect, with a substance provided on the solid phase beads, through a reaction or wash zone and either reacting said substance in said zone or washing said solid phase body in said zone. The reacting of said substance or the washing of the said solid phase body is achieved by contacting the elongate solid phase with a fluid, e.g. a liquid.

It may be that the solid phase synthesis is the synthesis of a polymer. The polymer may be a peptide, protein or polypeptide. The polymer may be a polynucleotide. The polymer may be a polysaccharide. It may be that the solid phase synthesis is the synthesis of a small molecule drug, or a hybrid of peptide, protein, polypeptide, polysaccharide, polynucleotide or small molecule.

The method typically comprises passing the elongate solid phase body through a plurality of reaction zones and/or a plurality of wash zones. Each reaction or wash zone performs a step of the solid phase synthesis.

The method may be a method of carrying out a solid phase synthesis as described in WO2009/004334 or WO2010/079349 (both incorporated herein by reference in their entirety) in which the elongate solid phase body of the first aspect is used in place of the elongate solid phases described in those disclosures. Typically, therefore, the reaction or wash zone comprises a conduit and the method comprises contacting the elongate solid phase body with a liquid in a conduit. It may be that the method comprises passing elongate solid phase body through a conduit from a first solid phase port to a second solid phase port; and causing the liquid comprising to enter the conduit of the reaction module through a first input port, flow through the conduit and leave through a second fluid output port. Where the zone is a reaction zone, the liquid comprises a reagent. Where the zone is a wash zone, the liquid typically does not comprise a reagent.

During each step, therefore, the solid phase body moves or is able to move; for example the movement of the solid phase body may be a movement which would for practical purposes be considered continuous (including continuous movement driven by a stepper motor, which in fact rotates in high frequency steps). In some embodiments, the solid phase body is stationary during performance of a step and then moved on to another apparatus to be subjected to another step. In other embodiments, the solid phase body moves intermittently during performance of a stage. The fluid phase flows during at least part of a step and it may flow continuously. Thus, the invention includes embodiments in which the solid phase body is contacted with, e.g. surrounded by, a stream of fluid during part or all of a step. A fluid may flow continuously during a step but in some embodiments fluid flow is discontinuous. In many embodiments, both the solid phase body and the fluid phase move continuously between the beginning and the end of a step.

It may be that the liquid flows in the opposite direction to the solid phase body.

The step of a solid phase synthesis may comprise the addition of a monomer unit to the species solid phase bead. Typically the beads will have linker group precursor groups, e.g. RINK linker group precursors, and the step may therefore be the addition, via covalent bond formation, of a first monomer unit to the linker precursor groups to form a monomer unit linked to the bead via a linker group. In this instance, a linker group precursor is the species attached to the solid phase bead and the reagent is the monomer unit, or an activated form thereof. Typically that first monomer unit will have one functional group (e.g. amino group, hydroxyl group, carboxylic acid group) free and a further functional group protected by a protecting group (e.g. fluorenylmethyloxycarbonyl (FMOC) or tert-butyloxy carbonyl (Boc) group for amines). This ensures that the desired functional group (the free functional group) forms the covalent bond with the linker group precursor.

The step of a solid phase synthesis may comprise the addition of a second or subsequent monomer unit to the species on the solid phase bead. In this instance, the species attached, typically via a linker group, to the solid phase bead is typically a monomeric, oligomeric or polymeric intermediate and the reagent is the monomer unit, or an activated form thereof. Again, typically the second or subsequent monomer unit will have one functional group (e.g. amino group, hydroxyl group, carboxylic acid group) free and a further functional group protected by a protecting group (e.g. FMOC group).

The step of the solid phase synthesis may comprise the removal of a protecting group from a monomeric, oligomeric or polymeric intermediate. This serves to liberate a functional group (e.g. an amine) on the oligomeric or polymeric intermediate for reaction with a subsequent monomer unit. In this instance, a protected monomeric, oligomeric or polymeric intermediate is the species attached to the solid phase bead and the reagent is an appropriate deprotection agent. Where the protecting group is an FMOC group, the reagent may be piperidine. Where the protecting group is Boc the deprotecting agent may be hydrogen fluoride or trifluoroacetic acid.

The step of the solid phase synthesis may comprise activation of a functional group on a monomeric, oligomeric or polymeric intermediate. This can increase the reactivity of the functional group, e.g. a recently deprotected functional group, to a subsequent monomer unit. Examples include the conversion of a carboxylic acid to an acid chloride or a mixed anhydride. In this instance, a protected monomeric, oligomeric or polymeric intermediate is the species attached to the solid phase bead, typically via a linker group, and the reagent is an appropriate activating agent.

It may be that the elongate solid phase body is subjected to ultrasound as it passes through said zone. This can improve the mixing between the solid phase beads and the fluid.

In a third aspect of the invention is provided a method of making the elongate solid phase body of the first aspect, the method comprising:
  depositing a plurality of predetermined portions of the solid phase beads periodically along
  a first elongate strip of the material;
  laying a second elongate strip of the material on the first elongate strip of material;
  connecting the two elongate strips of material such that they are connected continuously along both longitudinal sides of the elongate body and, at a position between the respective portions of solid phase bead, connecting the two elongate strips of material continuously across the transverse width of the elongate body to form the enclosures.

It may be that the two elongate strips are separate strips and connecting the two elongate strips of material such that they are connected continuously along both longitudinal sides of the elongate body comprises connecting the two elongate strips of material continuously along both longitudinal sides of the elongate body. It may be that the two elongate strips are a single piece of elongate material. In this embodiment, laying the second elongate strip on the first elongate strip comprises folding the piece of material to provide the two elongate strips of material connected along a first one of the longitudinal sides of the elongate body and connecting the two elongate strips of material such that they are connected continuously along both longitudinal sides of the elongate body comprises connecting the two elongate strips of material continuously along a second longitudinal sides of the elongate body.

Where the material is polymeric, the strips of material may be connected by welding, e.g. using an ultrasonic welder or using a continuous thermal welder.

Alternatively, the strips of material may be connected by sewing, stapling or bonding.

The seams or joins along the longitudinal edge or edges of the elongate body may be provided in such a way as to provide purchase for a roller.

Once formed, the elongate solid phase body may be rolled onto a spool.

The first elongate strip of the material may be supplied from a spool. The second elongate strip of the material may be supplied from a spool. The single piece of material that comprises both strips of elongate material may be supplied from a spool.

Any of the embodiments described above for the first aspect of the invention apply equally to the second and third aspects of the invention.

Figure 2:
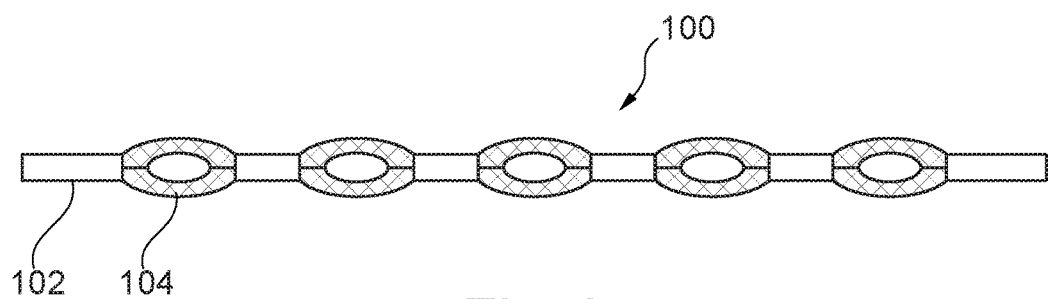
Figure 3:
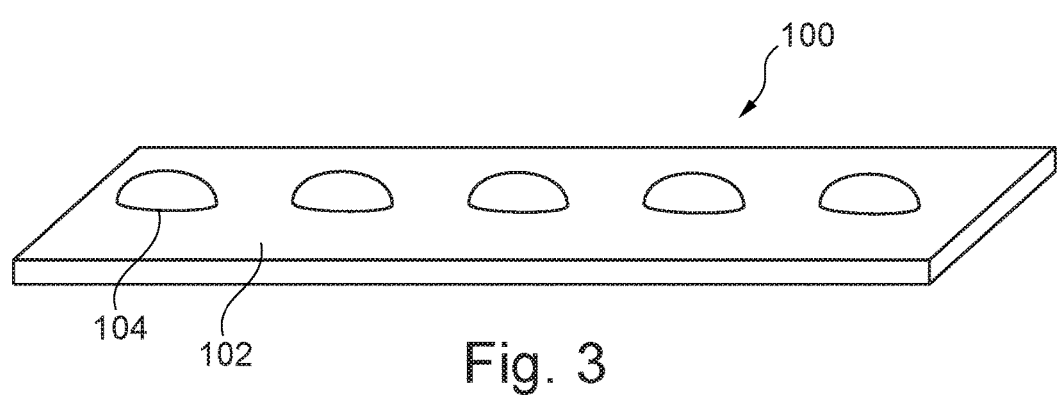
Figure 4:
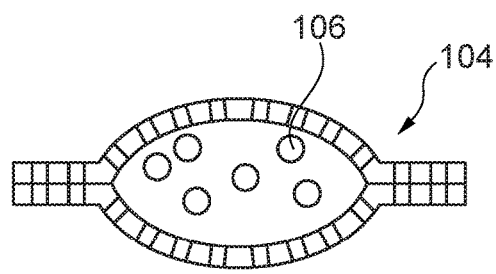
Figure 5A:
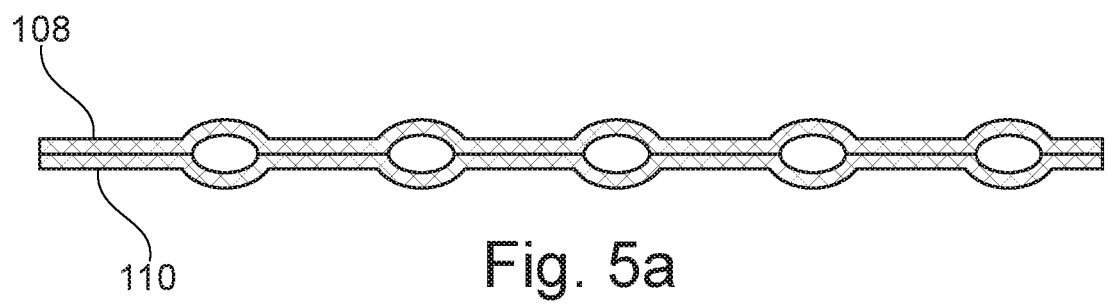
Figure 5B:
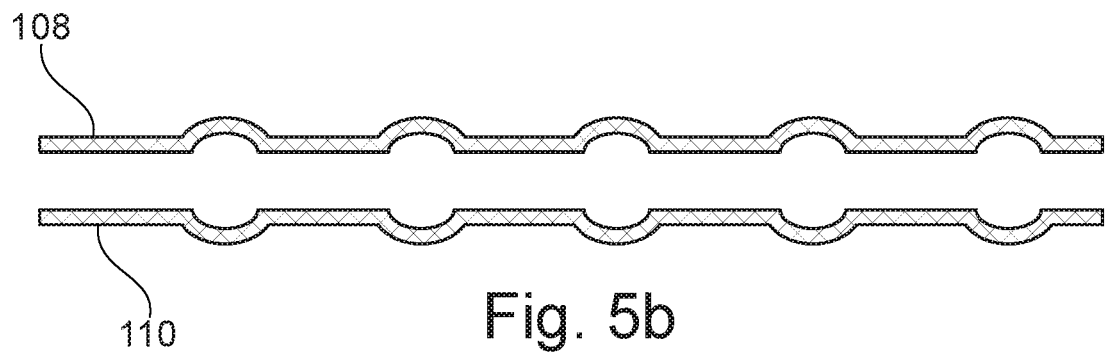

Embodiments of the invention are further described hereinafter with reference to the accompanying drawings, in which:

FIG. 1 illustrates a top view of an elongate body;
FIG. 2 illustrates a cut away view of the elongate body of FIG. 1 along the line A-A;
FIG. 3 illustrates a perspective view of the elongate body of FIGS. 1 and 2;
FIG. 4 illustrates a side view of an enclosure;
FIG. 5a illustrates another elongate body; and
FIG. 5b illustrates two strips of material used to form the elongate body of FIG. 5a.

In the drawings like reference numerals refer to like parts.

DETAILED DESCRIPTION

The term 'solid phase bead' is used herein to mean any particle which has or is capable of having a chemical species covalently attached thereto. The beads may be spherical but they may also be elliptical, cylindrical, cuboid or any other regular or irregular shape. Where the bead is not spherical, the 'diameter of the bead'. The 'diameter of the bead' is used herein to mean the cross-sectional length of the bead in the direction for which the cross-sectional length is shortest. The average diameter of a plurality of beads can be determined by, for example, determining the mass of a known number of beads, determining the total volume from the known bead material density, determining the volume of an average bead, then deem the diameter of a sphere with that average volume the mean diameter.

The species is typically a chemical species attached to the solid phase beads. The species may be a linker group, a first monomer unit or an oligomeric or polymeric intermediate in the synthesis of the desired polymer.

A linker group precursor is a chemical entity group which is attached to a solid phase bead and which has a functional group that is capable of reacting with a chemical substance such that the substance is attached to the solid phase bead via a linker group.

Throughout this specification, the term 'attached' is used herein to mean 'attached via covalent bonding'. Typically, 'attached' will mean 'cleavably attached via covalent bonding'. 'Cleavably attached' means that the substance is attached in such a way as to be cleaved by exposure to appropriate conditions, e.g. to an appropriate reactant.

The term 'plurality' means at least two. The elongate body of the invention may has at least two enclosures, each of which has within it at least two solid phase beads. It may be that the elongate body comprises at least 10 enclosures. It may be that the elongate body comprises at least 20 enclosures. It may be that the elongate body comprises at least 50 enclosures.

The term 'elongate' means that the length of the body is substantially longer than the width. It may be that the ratio of length to width of the body is at least 20:1. It may be that the ratio of length to width of the body is at least 50:1.

Solid Phase Synthesis

Solid phase synthetic methods have been extensively used in the preparation of a wide variety of compounds.

A useful review of the preparation of cellulose-bound peptide arrays is Hilpert K et al, Cellulose-bound peptide arrays: Preparation and applications, Biotechnol. Genet. Engineer. Rev. 2007, 24:31-106. Hilpert et al teach that cellulose is a polysaccharide with free hydroxy groups and that, since these hydroxy groups are less reactive than amino groups, the direct attachment of amino acids often leads to low yields. To make the cellulose suitable for the synthesis of peptides, the cellulose surface is modified to change the functionalisation from hydroxy to amino groups. It is further taught that modification of the cellulose often involves insertion of a spacer molecule permitting better access to the amino groups on the cellulose. After functionalisation, the amino acids are taught to be coupled either as an active ester (e.g. pentafluorophenyl ester) solution or as in situ activated mixtures. In situ activation is described as mostly carried out with DIC (N, N'-diisopropyl carbodiimide) and HOBt (N-hydroxybenzotriazole) shortly before coupling. Pages 34-42 of Hilpert et al are referred to here in particular as describing pre-treatment of the cellulose and peptide synthesis. Techniques for screening peptide arrays are described later in the same paper. Hilpert et al mention also non-cellulosic substrates (on page 33) and the synthesis of non-peptidic compounds (on page 43).

Mutulis F et al, J. Comb. Chem. 2003, 5:1-7 describe a method for producing non-random peptide libraries using cotton discs. The discs were activated in (25 v/v % in DCM) TFA (to protonate the hydroxy groups of the cotton). To enable peptide synthesis a handle was attached to the cotton to provide access to reagent molecule and a linker was then attached to the handle to provide a reactive site for Fmoc solid phase synthesis. The handle was 6-aminocaproic acid ($H_2N-(CH_2)_5-COOH$) and the linker was Fmoc Rink linker 4-[(2,4-dimethoxyphenyl)(Fmoc-amino)methyl]-phenoxyacetic acid. Peptides having different amino acid sequences were then synthesised on different discs.

The synthesis of oligonucleotide arrays on cellulose is described by Frank W et al, Nucl. Acids. Res. 1983, 11:4365-4377. Paper discs were pretreated by coupling protected nucleoside-3'-succinates were coupled to the discs by condensation of their carboxylic functions with the hydroxy groups of the cellulose in the presence of MSNT (1-(mesitylene-sulfonyl)-3-nitro-1,2,4,-triazole). After deprotection, a dimethoxy-tritylated base protected phosphodiester is coupled to the pretreated paper disc and further dimethoxy-tritylated base protected phosphodiester building blocks are linked step by step to form the completed oligonucleotide.

Fromont C et al, Chem. Commun. 2000, 283-284 describes the use of triple branching symmetrical dendrimers to increase the loading of a solid phase in the form of resin beads. The authors describe the synthesis of a tri-branching symmetrical dendrimer on the solid phase with an 18-fold amplification of loading. The tri-functional dendrimer monomers were prepared in bulk by alkylation of tris with acrylonitrile followed by nitrile hydrolysis in a saturated solution of HCl in dry MeOH to give the methyl ester. The hindered amino group of the methyl ester was converted to the corresponding isocyanate by treatment with $Boc_2O$ and DMAP as described by Knölker to give a stable symmetrical monomer (Knölker H-J et al, Angew. Chem., Int. Head. Engl. 1995, 34: 2497) an amino methyl polystyrene resin was directly derivatised with the isocyanate. The methyl ester was displaced by propane-1,3-diamine. The process was repeated to give Generation 2.0 dendrimer beads. The use of glass as a substrate for attachment of analytes or biological molecules is well known. For example, Millipore Data Sheet "DNA Nucleoside Controlled Pore Glass (CPG®) media" describes the use of DNA-CPG products for the solid phase synthesis of oligonucleotides using phosphoramidite chemistry. The data sheet is identified as Lit. No. DS0010EN00 Rev. A 03/06.

Shenoy N R et al, Protein Sci. 1992, 1:58-67 describes the use of carboxylic acid-modified polyethylene as a solid phase support for polypeptides. The peptides are attached by coupling the N-terminal amino group of the peptides to the activated carboxyl groups of the film. The carboxylic acid-modified polyethylene (PE-COOH film) was provided by the Pall Corporation of Long Island, N.Y. The highest yields of covalently attached peptide were obtained when 1,3-dicyclohexylcabrodiimide (DCC) was used as an activating agent.

It is also known to use so-called "CLEAR" resins (Cross-Linked Ethoxylate Acrylic Resin) as supports for solid phase peptide synthesis. Such CLEAR products are described in U.S. Pat. Nos. 5,910,554 and 5,656,707 and are produced by Peptides International, Inc.

Sanghvi Y S et al, Pure and Applied Chemistry, 2001, 73: 175-180 describe reusable solid support chemistries for oligonucleotide synthesis. The reusable solid support technology is based on the use of a hydroquinone diacetic acid spacer arm between the 3'-end of the first nucleoside and the hydroxyl-functionalised support. Details of the chemistry have been published in Pon R T et al, Nucleic Acids Research, 1999, 27: 15-31.

For a review article relating to developments in solid phase synthesis supports see Sucholeiki, Molecular Diversity, 1999, 4: 25-30. The new solid phase synthesis supports described include cross-linked polyoxyethylene-polystyrene and polyoxyethylene-polyoxypropylene and polyamidoamine dendrimers attached to TentaGel support.

The solid phase PEGylation of a protein has been described by Lee B K et al in Bioconjugate Chem., 2007, 18: 1728-1734. Recombinant interferon α-2a was absorbed to a cation exchange resin and PEGylated at the N-terminus by mPEG aldehydes through reductive alkylation using $NaBH_3CN$ as reducing agent.

An increasingly important class of polymer is organic semiconductor polymers. Turner D et al, Mat. Res. Soc. Symp. Proc., 2003, 771: L8.8.1-L8.8.5 describe a solid phase synthetic strategy for the production of organic semiconductors. The strategy uses a germanium-based linker and Suzuki-type cross-coupling protocols and has been demonstrated for the iterative synthesis of both a regio-regular oligo-3-alkylthiophene and an oligoarylamine. Turner et al is included herein in its entirety for all purposes, as are references 1, 2, 3 and 4 of Turner et al.

For further information on solid phase synthesis techniques, reagents and substrates see Organic Synthesis on Solid Phase: Supports, Linkers, Reactions, Florencio Zaragoza Dörwald, Wiley-VCH, Second Edition, 2002, ISBN 352730603X.

Solid Phase Body

An elongate solid phase body 100 suitable for solid phase synthesis (e.g. as mentioned above) is shown in FIGS. 1-3. The elongate body in this case can be said to be similar to a ribbon, having a length substantially longer than its width and having flexibility to be moved around a pathway of a reaction module, or other reaction system.

The body 100 includes an elongate body portion 102. The body portion is a strip that forms the shape of the ribbon. In this case the body portion is of mesh material. The ribbon is, in this example, 1000 mm long×22 mm across×2 mm depth.

The body portion has discrete cut out areas along the length of the body portion (in this case circular shaped). Filling each of the cut out areas, there are a plurality of enclosures 104. Thus, the enclosures are distributed along the length of the elongate body portion. The enclosures are formed of a material including a chemically inert mesh. In this case the enclosure is a mesh of ethylene tetrafluoroethylene copolymer (ETFE) with cross woven threads of 50 micron diameter.

As shown in FIG. 4, the enclosure 104 may be formed from two sheets of mesh that are joined at the edges creating a pouch type of enclosure. The edges of the enclosure are connected to the body portion to form a continuous ribbon.

As an alternative arrangement, as shown in FIGS. 5a and 5b, the elongate body 200 may include two elongate strips of ETFE 108, 110 connected together at opposing faces at various portions. When viewing the elongate body in plan view (as per the view of FIG. 1), the two strips of material 108, 110 are connected continuously along both longitudinal sides of the strips and are also periodically connected continuously across the transverse width of the elongate body. With this arrangement the enclosures are formed by the non-joined areas of the two elongate strips. The strips of material 108, 110 may be entirely formed of ETFE mesh (as represented in FIGS. 5a and 5b), or may be formed from a variety of materials with a chemically inert mesh at the area of the enclosures.

The two strips may be joined by heat treatment of the ETFE or by use of an adhesive, or by a mechanical attachment, etc.

Within each enclosure 104, there is provided a plurality of solid phase beads 106. In this case the beads are a polyethylene glycol polystyrene hybrid resin, and the solid phase beads have linker group precursors attached to them.

The size of the holes in the mesh and the size distribution of the solid phase beads are selected such that the beads do not pass through the mesh. In certain particular embodiments, the thickness of the pores in the mesh is in the range from 50 μm to 60 μm and the beads have a minimum size of 65 μm.

With the above described embodiment, the plurality of enclosures function to carry a solid phase (in the form of beads), to be used for a reaction process.

Various modifications to the detailed arrangements as described above are possible. For example, the elongate body is not limited to the specific size and shapes described above. The elongate body may be designed to suit a particular application of use for a particular reaction system, for example.

The arrangement of enclosures (sequential pouches as above) may be provided in a number of arrangements, for example in sets of two (or more) adjacent enclosures sequentially along the elongate body.

Optionally, a reinforcing element, e.g. glass fibre, may be provided along the longitudinal edges of the elongate body. The reinforcing element will typically be chemically inert. The reinforcing elements may be welded or sewn or mechanically or chemically attached to the body portion, or may be formed integrally with the body portion, e.g. of higher thread count or denser/higher strength fibre. The reinforcing elements may be useful to provide additional strength to the body for passing through a reaction system. Each reinforcing strip may be a portion of the material or mesh, situated along the respective longitudinal side of the elongate body portion, which has a higher thread count than the rest of the material of mesh. Each reinforcing strip may be a seam. Each reinforcing strip may be a elongate piece of material or fibre that is connected to or embedded in the material or mesh along the respective longitudinal edge. The fibre may be formed of aramid or glass.

Optionally, the elongate solid phase may include an identity marker. Inclusion of a single marker can allow the ribbon to be individually identified, e.g. to identify batch numbers and/or for quality control purposes. The marker may be a barcode printed on the elongate solid phase body. Alternatively the marker may be an RFID tag or microchip embedded in the elongate solid phase body.

Optionally, the elongate solid phase may include, situated at regular intervals along its length, a plurality of markers. These markers allow the passage of the ribbon through the solid phase reaction system to be monitored. The markers may be visible markers, the markers may be magnetic markers or the markers may be electronic markers. Typically the markers will be placed so that they can be detected by an appropriate sensor as the elongate solid phase body moves past.

It may be that each marker is individually identifiable. Thus, the markers may be barcodes printed on the elongate solid phase body. Alternatively the markers may be RFID tags or microchips embedded in the elongate solid phase body.

It may be, on the other hand, that the plurality of markers are the same. Such markers can be used to measure the speed of the elongate body through one or more portions of an apparatus. Examples of such markers include simple geometrical marks (e.g. spots) that can be detected by an appropriate detector. The marks may be contrasting in colour to the material of the elongate body. Where the elongate body is light coloured, the marks may be black or other dark colours and vice versa. The marks may be detectable by UV spectroscopy.

The elongate solid phase body may comprise both an identity marker and a plurality of markers that allow the passage of the ribbon through the solid phase reaction system to be monitored. Where each of the plurality of markers is individually identifiable, it may be that the markers can be used to identify the elongate solid phase and/or a section of the elongate solid phase.

In the systems of the invention, it is generally not needed to have a marker at every enclosure. Thus, it may be that the number of markers on the elongate body is less than 50% of the number of enclosures. It may be that the number of markers on the elongate body is less than 20% of the number of enclosures. It may be that the number of markers on the elongate body is less than 10% of the number of enclosures.

With the present invention, the solid phase (beads), for use in a reaction, is separated from a carrier (the elongate body). In previous known arrangements, the elongate body itself was the solid phase for reaction processing. This separation allows for various advantages.

The new elongate solid phase has the mechanical and chemical components split into different materials and thus avoids trade-offs in performance that were observed with the prior art solid phases. Thus, the mesh may be selected to be chemically unreactive when subjected to the desired reaction conditions of any given reaction step, e.g. cleavage steps involving strong acids.

The use of a mesh encapsulating the beads provides a much higher void space than in prior art elongate solid phases, allowing better mixing of fluid into the solid phase.

Furthermore, the beads are free to move within the enclosures under ultrasound application giving better mixing than the restricted matrix of a woven cellulose ribbon to increase the rate of the reactions. The solid phase beads also have room to increase in size during the synthesis.

The design is flexible and can allow for the inclusion of any desired solid phase beads.

The mesh contains the solid phase beads in distinct enclosures, thereby allowing a particular portion to be reacted at a particular time and preventing longitudinal migration of the beads. This may lead to fewer impurities compared to solids phases in which the beads are placed in an elongate enclosure.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An elongate solid phase body for solid phase synthesis, the elongate solid phase body comprising:
    an elongate body portion and enclosures distributed along the length of the elongate body portion, the enclosures being formed of a material comprising a chemically inert mesh; and
    within each enclosure, solid phase beads;
    wherein the size of the holes in the mesh and the size distribution of the solid phase beads are selected such that the beads do not pass through the mesh;
    wherein each enclosure contains less than 90% of the maximum amount of the solid phase beads that the enclosure can hold;
    wherein the enclosures contain an amount of solid phase beads selected such that the solid phase beads have room to increase in size during the synthesis and the solid phase beads are free to move within the enclosures during the synthesis;
    wherein the elongate solid phase body comprises two elongate strips of the material connected together so as to form the elongate body portion and the enclosures; and
    wherein the two elongate strips are periodically connected continuously across the transverse width of the elongate body portion to form the enclosures.

2. The elongate solid phase body of claim 1, wherein the two elongate strips are further connected continuously along both longitudinal sides of the two elongate strips.

3. The elongate solid phase body of claim 1, wherein the mesh is a polymeric mesh.

4. The elongate solid phase body of claim 3, wherein the polymer is polyether ether ketone (PEEK).

5. The elongate solid phase body of claim 3, wherein the polymer is a fluorinated polymer or copolymer.

6. The elongate solid phase body of claim 1, wherein the solid phase beads are polymer beads.

7. The elongate solid phase body of claim 6, wherein the solid phase beads are a polyethylene glycol polystyrene hybrid resin.

8. The elongate solid phase body of claim 7, wherein the solid phase beads are a polystyrene divinylbenzene hybrid resin.

9. The elongate solid phase body of claim 1, wherein the solid phase beads have linker group precursors attached to them.

10. The elongate solid phase body of claim 1 further comprising an identity marker.

11. The elongate solid phase body of claim 1 further comprising, situated at regular intervals along its length, a plurality of markers.

12. A method of performing a solid phase synthesis comprising:
    passing the elongate solid phase body of claim 1, with a substance provided on the solid phase beads, through a zone; and
    either:
        reacting the substance in the zone; or
        washing the elongate solid phase body in the zone by contacting the elongate solid phase body with a liquid.

13. The method of claim 12, wherein the solid phase synthesis is the synthesis of a polymer selected from the group consisting of a protein, peptide and polypeptide.

14. The method of claim 12, wherein the solid phase synthesis is the synthesis of a polynucleotide.

15. The method of claim 12, wherein the zone is selected from the group consisting of a reaction zone and a wash zone;
    wherein the zone comprises a conduit; and
    wherein the method further comprises contacting the elongate solid phase body with the liquid in the conduit.

16. The method of claim 12, wherein passing the elongate solid phase body through a zone comprises passing the elongate solid phase body through a plurality of zones.

17. The method of claim 12 further comprising subjecting the elongate solid phase body to ultrasound as it passes through the zone.

18. A method of making the elongate solid phase body of claim 2 comprising:
- depositing predetermined portions of the solid phase beads periodically along a first elongate strip of the two elongate strips;
- laying a second elongate strip of the two elongate strips on the first elongate strip;
- connecting the two elongate strips such that the two elongate strips are connected continuously along both longitudinal sides of the elongate body portion; and
- at a position between the respective portions of solid phase bead, connecting the two elongate strips continuously across the transverse width of the elongate body portion to form the enclosures.

19. The elongate solid phase body of claim 1, wherein the solid phase beads are controlled porosity glass beads.

20. The elongate solid phase body of claim 2, where the two elongate strips form a single piece of the material that is folded along a first longitudinal side of the elongate body portion and sewn, stapled or bonded continuously along the second longitudinal side of the elongate body portion.

21. The elongate solid phase body of claim 2, where the two elongate strips are sewn, stapled or bonded continuously along each longitudinal side of the elongate body portion.

* * * * *